United States Patent [19]
Kosugi et al.

[11] Patent Number: 5,292,649
[45] Date of Patent: Mar. 8, 1994

[54] METHOD FOR REACTION OF LIPASE UPON FATTY ACID

[75] Inventors: Yoshitsugu Kosugi, Yatabemachi; Hideo Suzuki, Tokyo; Akio Sato, Ibaraki, all of Japan

[73] Assignee: Agency of Industrial Science & Technology, Ministy of International Trade & Industry, Tokyo, Japan

[21] Appl. No.: 912,655

[22] Filed: Jul. 9, 1992

Related U.S. Application Data

[63] Continuation of Ser. No. 614,040, Nov. 13, 1990, abandoned, which is a continuation of Ser. No. 243,131, Sep. 9, 1988, abandoned, which is a continuation of Ser. No. 839,536, Mar. 14, 1986, abandoned, which is a continuation-in-part of Ser. No. 586,563, Mar. 6, 1984, abandoned.

[30] Foreign Application Priority Data

Mar. 29, 1983 [JP] Japan ................................. 58-53285

[51] Int. Cl.$^5$ ............................................. C12P 7/40
[52] U.S. Cl. .................................... 435/136; 435/134; 435/135; 435/177; 435/178; 435/179; 435/180; 435/181; 435/182
[58] Field of Search ............... 435/136, 134, 180, 181, 435/182, 177, 178, 179, 159, 198, 271, 35

[56] References Cited

U.S. PATENT DOCUMENTS

| | | | |
|---|---|---|---|
| 3,915,797 | 10/1975 | Ishimatsu et al. | 435/180 |
| 4,170,696 | 10/1979 | Hirohara et al. | 435/180 |
| 4,205,128 | 5/1980 | Ishimatsu et al. | 435/182 |
| 4,275,081 | 6/1981 | Coleman et al. | 426/33 |
| 4,451,582 | 5/1984 | Denzinger et al. | 435/188 |
| 4,798,793 | 1/1989 | Eigtved | 435/134 |
| 4,818,695 | 4/1989 | Eigtved | 435/134 |

OTHER PUBLICATIONS

Merck Index, 10th ed., p. 981 (1983).
English language translation of the abstract of Japanese Patent Publication 54–76892, 1979.
English language translation of the abstract of Japanese Patent Publication 56–50554, 1981.

*Primary Examiner*—Carolyn Elmore
*Assistant Examiner*—Shailendra Kumar
*Attorney, Agent, or Firm*—Oblon, Spivak, McClelland, Maier & Neustadt

[57] ABSTRACT

The reaction of a lipase upon a fatty acid is effected by an improved method which comprises bringing the lipase bonded at multiple points to an anion-exchange residue or a carrier and a carrier having a free anion-exchange group admixed therewith into contact with a reaction mixture containing an oily substance including the fatty acid and a water-soluble substance thereby forming an oily product and a water-soluble product in the reaction mixture and subsequently separating the two reaction products.

6 Claims, 1 Drawing Sheet

METHOD FOR REACTION OF LIPASE UPON FATTY ACID

CROSS-REFERENCE TO RELATED APPLICATIONS

This application is a continuation of application Ser. No. 07/614,040, filed on Nov. 13, 1990, now abandoned which is a continuation of Ser. No. 07/243,131, filed on Sep. 9, 1988, now abandoned, which is a continuation of Ser. No. 06/839,536, filed on Mar. 14, 1986, now abandoned, which is a continuation-in-part of Ser. No. 06/586,563, filed on Mar. 6, 1984, now abandoned.

FIELD OF THE INVENTION AND RELATED ART STATEMENT

This invention relates to an improvement in and concerning the reaction of a lipase upon a fatty acid, and more particularly to an improved method which comprises bringing a reactant mixture containing an oily substance including a fatty acid therein into contact with a carrier incorporating therein a free anion-exchange residue and an immobilized lipase, said immobilized lipase being bonded in at least one form of bonding selected from the group consisting of ionic bonding, hydrophobic bonding and covalent bonding to said carrier at multiple points, thereby forming an oily product and a water-soluble product in the reaction mixture and separating the products from the reaction mixture.

The lipase is an enzyme which acts upon ester bonds and, therefore, is useful for ester hydrolysis, ester synthesis, or transesterification. It is also an enzyme which is made to act upon racemic esters, acids, and alcohols for the purpose of optical resolution. A. M. Klivanov et al. have demonstrated that an immobilized lipase obtained by fixing the lipase of *Candida cylindracea* in a macroreticular porous hydrophobic carrier called Chromosorb is useful. They have not given any solution to the factors inhibiting the reaction of a fatty acid. They have made the following statement.

"Hydrolases have been successfully used for the production of esters from alcohols and carboxylic acids. However, careful examination of these studies shows that they either have been carried out at very low concentrations of the acid (1 mM~10 mM) or that the degree of utilization of the enzyme was low. The inherent drawback associated with esterase-catalyzed esterifications is biphasic systems in a drop in the pH brought about by addition of the acid. The higher the concentration of the acid (which is imperative for preparative productions), the more severe this problem becomes. One could continuously adjust the pH if the reaction were carried out in a monophasic aqueous system but then the equilibrium is usually not in favor of esterification." [B. Cambau and A. M. Klivanov, Biotechnol. Bioeng., 26, 1449 (1984)]

In the reaction of a soluble lipase, as the pH value of the reaction mixture is lowered by the fatty acid, further progress of the reaction is heavily retarded. Efforts to improve the progress of the lipase reaction by keeping the pH of the reaction mixture at its optimum level by continuing the addition of an alkali to the reaction mixture as regulated with the aid of a pH stat have failed. The reason for this failure may be that the added alkali reacts with the produced fatty acid to give rise to a surface active agent and this surface active agent denatures the lipase protein.

OBJECT AND SUMMARY OF THE INVENTION

The inventors made a study in search of a way of eliminating the obstacles to the practical adoption of the aforementioned method of prior art. It has been consequently ascertained to them that the lipase is stabilized when it is bonded at multiple points to a carrier, that with respect to the decrease of the pH caused by the fatty acid, the lipase activity can be manifested amply by using an immobilized lipase prepared by a new method capable of permitting presence of a multiplicity of anion-exchange residues on the surface of a carrier having lipase bonded thereto and further by causing the pH of the microenvironment enveloping the lipase to be shifted by the electrostatic repulsion of the anion exchange residue toward the alkaline side without necessitating addition of an alkali or calcium carbonate in spite of the presence of the fatty acid, and that the factors inhibiting the progress of the reaction can be eliminated and the fractional separation of the oily product and the water-soluble product can be materialized by making effective use of the specific gravity and the hydrophobicity of the fatty acid. The present invention has been perfected on the basis of this knowledge.

The term "multiple point bonding" as used herein means that the lipase is bonded to the carrier at two or more points on the carrier per molecule of the lipase.

This invention is directed to an improvement in and concerning the reaction of a lipase upon a fatty acid. It can be applied not only to ester synthesis and transesterification by the use of a fatty acid but also to ester hydrolysis for producing a fatty acid in a large amount as a reaction product.

BRIEF DESCRIPTION OF DRAWING

The drawing illustrates the structure of an apparatus used in Examples 6 and 7.

DETAILED DESCRIPTION OF PREFERRED EMBODIMENTS

Figure 1:
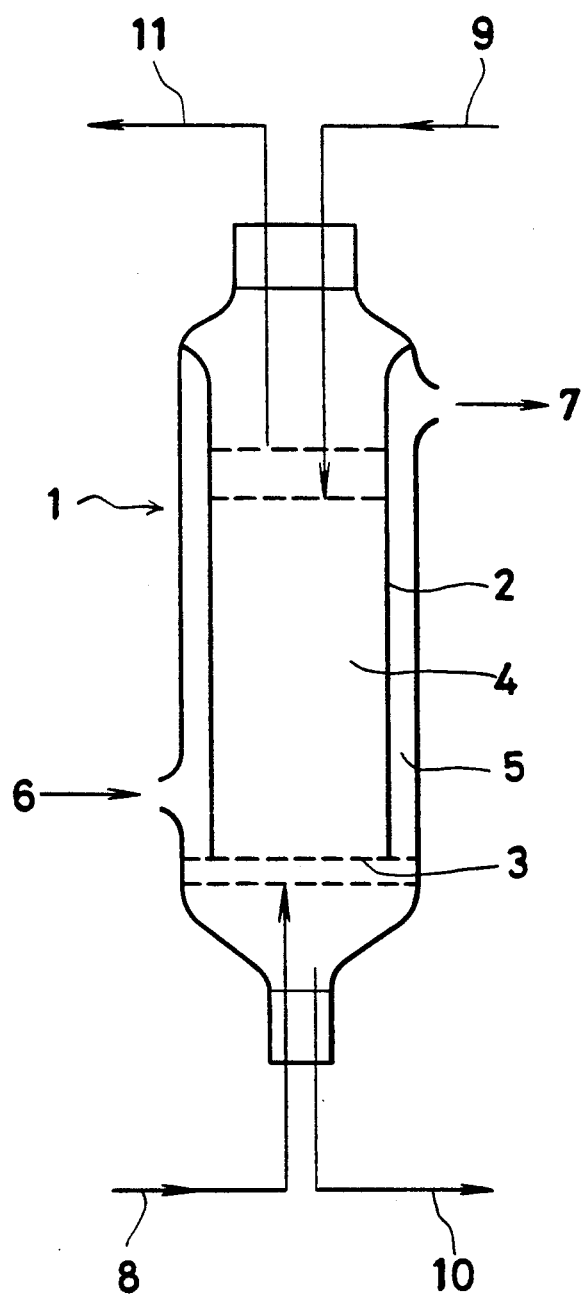

This invention does not discriminate among lipases to be used, particularly by the source thereof. The enzyme nevertheless is desired to have high affinity as for a lipid and begin to react upon the substrate rapidly. When the lipid to be hydrolyzed is a fat of high melting point such as tallow, it is desirable to use a thermostable lipase which is capable of reacting at a temperature exceeding 45° C.

An example of an enzyme of the former description is the lipase produced by *Candida cylindracea* (Benzonana G., Esposito S. (1971) Biochim. Biophys. Acta 231, 15). An example of an enzyme of the latter description is the lipase produced by *Pseudomonas mephitica* var. *lipolytica* (Kosugi Y., Kamibayashi A. (1971) J. Ferment. Technol. 49; 968).

For the purpose of optical resolution of racemic compounds and formation of monoglyceride, a lipase of the type capable of giving a product of high optical purity and a lipase of the type possessing specificity with respect to the α position of glyceride are used. For example, the lipase of *Penicillium cyclopium* (S. Okamura, M. Iwai, and Y. Tsujisaka, J. Biochem, 87, 205–211 (1980) is usable for the production of monoglyceride.

Examples of carriers usable for this invention include various anion-exchange resins, glass beads and silica beads having anion-exchange residues introduced therein through the medium of silan coupling reagents, metal powders having anion-exchange residues introduced therein, hydrophilic vinyl polymers, celluloses, and agaroses having anion-exchange residues introduced therein through the medium of hydrophobic spacers, porous entrapped gels having anion-exchange residues attached to the inner surfaces thereof, and membranes and hollow fibers having anion-exchange residues attached to the surfaces thereof.

The carrier to be adopted is desired to be hydrophobic because such a carrier exhibits better affinity for the lipid, permits better diffusion of lipid into the carrier, and provides better expulsion of hydrophilic glycerin and other water-soluble products formed in consequence of the reaction than when the carrier is hydrophilic. In the case of a reaction mixture containing glycerin in extremely high concentrations, when the carrier is hydrophobic, the carrier may permit only inferior diffusion of water-soluble substances. Particularly desirable results are obtained by using a macroreticular porous anion-exchange resin, glass beads or silica beads having an anion-exchange residue incorporated therein. This is because use of a porous carrier having pores whose average radius is about 10-100 times the average radius, 10 to 100 Å, of ordinary lipase molecules enables a given lipase to be bound to the surface inside the pores of the carrier, thus providing a very large area for the binding of lipase and improving diffusion of lipid within the carrier. The average pore radius of the carrier is not desired to exceed the level of 10000 Å, because the pore surface area available for the binding of lipase and anion-exchange residue decreases as the average pore radius of the carrier exceeds this level. The carrier to be used, therefore, has an average pore radius of 100 to 10000 Å. A macroreticular porous carrier has a large surface area for binding lipase even without being divided into fine particles. Use of such a carrier, therefore, makes possible preparation of an immobilized enzyme column not susceptible to any noticeable head loss.

The term "anion-exchange residue" as used in this invention is meant to embrace residues of various amines, ammonium compounds and derivatives thereof. These are chemical residues which, in a reactant mixture, are dissociated and positively charged, in which state they expel cations.

The carrier used for this invention has the anion-exchange residue bound thereto and also has a lipase immobilized on the surface of the carrier. On the surface of the carrier, therefore, the anion-exchange residue and the lipase occur as coexisting together. For the carrier to function with optimum effectiveness the density of the anion-exchange residue bound to the surface of the carrier should be as large as possible.

When the amount of lipase bound to the carrier is very small, the activity of the immobilized lipase, namely, the immobilized enzyme activity, is insufficient. In other words, the reaction by the immobilized lipase does not reach its maximum with sufficient rapidity. When the amount of the bound lipase is excessive, the reaction rapidly rises to maximum. The reactivity may become poor, however, when the fatty acid concentration in the reactant mixture is high. Since the lipase is often bound through the medium of the anion-exchange residue, it will be bound to all the anion-exchange residue when the amount of bound lipase is excessive. In this case, the anion-exchange residue will not be present in an exposed manner on the surface of the carrier. To maintain the reactivity at a high level with a reactant mixture having a high fatty acid concentration, it is necessary to use a carrier having amply bound thereto an anion-exchange residue generally of a low molecular weight and to adjust the amount of the lipase bound to the carrier so that the lipase will be bound barely in a monolayer to the surface of the carrier.

The lipase as a molecule is a polypeptide formed by the combination of more than 100 amino acids. In the light of the molecular weight of an amino acid, it suffices to immobilize such a number of molecules of lipase as not to exceed one thousandth of the total exchange capacity of an anion exchanger calculated on the basis of an anion having a low molecular weight. This number of molecules represents a magnitude such that more than 1000 anion-exchange residues will occur along the periphery of one molecule of lipase. In fact, in the gradual increasing of the amount of lipase bonded to an ion exchanger, there exists a point at which the amount of lipase in the wash suddenly increases as shown in Experiment 1. The immobilization mentioned above can be attained, therefore, by keeping the amount of lipase so bound below the amount of this particular point.

Since lipase is generally an acid protein, it is readily bound to the anion-exchange carrier through ionic bonding. When the carrier to be used happens to be a hydrophobic substance possessing an anion-exchange residue, the lipase is strongly bound to the carrier through both ionic bonding and hydrophobic bonding. The attachment of the lipase to the carrier is further enhanced when the carrier having the lipase immobilized thereon through ionic bonding and hydrophobic bonding is treated with a polyfunctional reagent such as, for example, glutaraldehyde, hexamethylene diisocyanate, or carbodiimide. In the case of the treatment made with glutaraldehyde, the glutaraldehyde is improved in reactivity and the lipase may be inactivated when the pH value exceeds 7. This treatment, therefore, is desired to be carried out at a temperature below 25° C. for a short period of about 10 to 20 minutes, with the pH adjusted in the neighborhood of 4.5 to 6.5. After this treatment, any excess glutaraldehyde should be removed with sodium hydrogen sulfite, for example. When the lipase molecules are bound at multiple points to the carrier as mentioned above, the ability of the lipase protein to resist changes of pH and temperature and the action of a protein denaturant is enhanced.

One typical method for the manufacture of an immobilizied enzyme column having a lipase fixed on a hydrophobic carrier to which an anion-exchange residue has been bound comprises allowing a suitable amount of a lipase solution to flow down a resin with a hydrophobic carrier possessing an anion-exchange residue thereby fixing the lipase to the carrier through ionic bonding and hydrophobic bonding, then allowing a suitably diluted glutaraldehyde solution of adjusted pH and temperature to flow down the resin, and thereafter passing a sodium hydrogen sulfite solution through the resin.

In the present invention, the pH and temperature conditions for the reaction of a lipase upon a fatty acid can be suitably determined by the kind of the immobilized lipase. For the lipase to manifest its ability to effect ester synthesis or transesterification, the water content in the reaction environment is desired to remain in the range of 0.5 to 3.0 w/w %. This range represents an intermediate between the water content necessary for keeping the lipase suitably hydrated and enabling it to manifest activity and the water content necessary for preventing hydrolysis from occurring conspicuously.

The reaction tolerates metal ion, serum albumin, etc. incorporated optionally in the reaction mixture.

The fatty acids that are effectively usable for this invention include both linear fatty acids and branched fatty acid. Any of these fatty acids can be used for this invention on the condition that it should be capable of interacting with the lipase. The fatty acid which is contained as a reaction product in the reaction mixture is also usable for this invention. When a triglyceride having a molecular weight of about 900 is completely hydrolyzed, there are formed one molecule of glycerin having a molecular weight of 92 and three molecules of a fatty acid having a molecular weight of about 270. Therefore, the hydrolysis produces not more than 10 w/w % of glycerin and more than 10 w/w % of fatty acid. In the present invention, the hydrolysis of fat in a high concentration is possible because the aforementioned products of hydrolysis do not discernibly inhibit the reaction as shown in Experiment 2.

In commercial production of a fatty acid, the oil phase and the aqueous phase (sweet water containing glycerin, etc.) which occur after the completion of the hydrolysis of a fat are separated from each other and the oil phase is further fractionated by crystallization into crude liquid fatty acid and solid fatty acid. These fatty acids are put to further purification. At times, unaltered triglyceride persists in the crude liquid fatty acid besides oleic acid and linoleic acid. Where the unaltered triglyceride remains in a concentration of about 8%, for example, in the crude fatty acid in hydrolyzing the unaltered triglyceride, water is also still contained in the crude fatty acid. The triglyceride still dissolved in the crude fatty acid as an extraneous component, therefore, can be removed by causing this crude fatty acid to react with the immobilized lipase. When the lipase is used in its free form, the activity of the lipase is seriously inhibited in the presence of the fatty acid. Such inhibition of the activity is not encountered even in the presence of a fatty acid when the removal of the residual triglyceride is effected by the use of the immobilized lipase contemplated by this invention. The use of this immobilized lipase shifts the optimum pH to the pH level at which the fatty acid is generally dissociated. Also in this respect, the immobilized enzyme of this invention has a notable effect.

As examples of the reaction device to be used for working the present invention, there may be cited a column packed with the immobilized lipase and a membrane or a hollow fiber having a lipase bound to its surface in coexistence with anion-exchange residue. When any of these reaction devices is adopted, the reactant mixture may be continuously passed. Simple mixture of the immobilized lipase with the reactant mixture serves to effect the hydrolysis batchwise. Because of its simplicity, this batchwise reaction may be used in combination with continuous separation of the products of reaction. No matter whether the reaction is performed batchwise or continuously, the recovery of the immobilized lipase from the reaction mixture is easily effected. After the reaction, the lipase protein does not contaminate the products. The immobilized lipase recovered from the reaction mixture can be put to use repeatedly. The continuous reaction has an advantage that the unsaturated fatty acid does not undergo oxidation because the reaction system is exposed only minimally to the ambient air. By separating the oily substance and the water-soluble substance in the reaction mixture and bringing them into countercurrent contact with the immobilized lipase, continuous fractional separation of the oily product and the water-soluble product by virtue of their differences in specific gravity and hydrophobicity can be materialized in conjunction with the continuous reaction of the lipase. This method improves the effects of the inhibition of the reaction products and the suspension of the reaction due to reaction equilibrium because the products are continuously separated from the reaction mixture. Further, the mean residence time of the oily substance and that of the water-soluble substance in the reaction vessel can be set independently of each other. It is made possible during a hydrolysis of fat to obtain a water-soluble product containing glycerin in a high concentration. The term "means residence time" as used herein means the quotient of the inner volume of the reaction vessel divided by the volume of the substance supplied to the reaction vessel during a definite length of time.

A column reactor for countercurrent contact is a vertically erect column provided each in the upper middle level, the lower middle level, the upper end, and the lower end thereof with an outlet and an inlet. Here, the upper middle level means the level which intervenes between the upper end and the middle between the upper and lower ends and the lower middle level means the level which intervenes between the middle mentioned above and the lower end. When the reaction products separate into two or more layers in the column reactor, fractional separation of such reaction products can be materialized by forming recovery ports one each in the levels of the column corresponding to the heights of the separated layers. The column reactor is operated by feeding the oily substance through the lower middle level and the water-soluble substance through the upper middle level respectively into the reactor and drawing the oily product through the upper end and the water-soluble product through the lower end respectively out of the reactor. In the column reactor for countercurrent contact, since the oil-water separation consumes much time, use of a slender column for the reactor does not prove proper but use of a short column divided into multistage columns proves advantageous.

When the column reactor is operated by the contact of a fatty acid with the immobilized lipase, the separation of the oily product and the water-soluble product due to their difference in hydrophobicity can be facilitated by addition of such a nonpolar solvent as isopropyl ether, hexane, isooctane, cyclohexane, pentane, or heptane to the reation mixture. In this case, therefore, the reaction can be continued simultaneously with continued removal of the products.

In the present invention, since the factors inhibiting the progress of the reaction of the lipase with a fatty acid are eliminated without use of any alkali and, therefore, the denaturation of protein and the increase of the water content in the reaction mixture are consequently precluded, this invention ideally fits a continuous operation of transesterification and ester synthesis in a system of a meager water content, or ester hydrolysis in a system of a high substrate concentration. Moreover, the immobilized lipase has a great advantage because of a stabilization derived from its immobilization. The operation which utilizes gravity and hydrophobicity of the fatty acid has the effect of enabling continuous fractional separation of the oily product and the water-soluble product as well as continuous reaction. It constitutes itself an excellent method of commercial reaction of the lipase with a fatty acid.

Now, the present invention will be described more specifically below with reference to experiments and working examples.

EXPERIMENT 1

One (1) gram of Dowex MWA-1 (a macroreticular porous type weakly basic anion-exchange resin having a tertairy amine introduced as an exchange group into a matrix having a polystyrene chain cross-linked with divinyl benzene of total exchange capacity of not less than 1.2 meq/ml produced by the Dow Chemical Company) was washed with distilled water and a 1/15M McIlvaine buffer of pH 5.0 and subsequently shaken with 5 $\mu$l of a lipase solution and 1 ml of McIlvaine buffer at 8° C. overnight. It was then shaken with 1 ml of McIlvaine buffer and 80 $\mu$l of a 25% glutaraldehyde solution at 8° C. for 10 minutes to enhance the binding of lipase to the Dowex MWA-1. Finally, the resultant reaction mixture was shaken with 0.2 ml of a 20% sodium hydrogen sulfite solution at 8° C. for 10 minutes to expel excess glutaraldehyde. It was then thoroughly cleaned with water and a buffer, to give rise to an immobilized lipase on Dowex MWA-1.

The lipase activity was determined as follows: A tributyrin emulsion was obtained by mixing 3.14 g of tributyrin, 35 ml of 2% polyvinyl alcohol (Kurashiki Poval 117) solution, 40 ml of 0.1M phosphate buffer of pH 7, and 12 ml of water and treating the resultant mixture with ultrasonic waves for 10 minutes. Then 9 ml of this tributyrin emulsion was mixed with 1 g of a lipase suspension and the resultant mixture was shaken at 60° C. for 20 minutes to effect reaction. The reaction thus caused was stopped by addition of a 1:1 mixture of methanol and acetone. The activity was determined by titrating the resultant fatty acid with a 0.05N NaOH solution. The amount of a given enzyme which liberated 1 microequivalent of an acid in one minute under the reaction conditions described above was defined as one unit.

The sample lipase was produced by *Pseudomonas fluorescens* biotype I-No. 1021 (Bikoken Deposit FERM-P No. 5495 dated Apr. 22, 1980; Budapest Treaty Deposit No. FERM BP-494 dated Mar. 1, 1984) obtained by salting out the lipase with ammonium sulfate, dialyzing the precipitated lipase, and lyophilizing the dialyzate, and defatting the lyophilized preparation. The lipase activity of this sample was 393 per mg of protein. Since a highly refined sample is found to possess lipase activity on the order of 2500 per mg of protein, it is logical to conclude that lipase protein in the sample accounts for about 16% of the total protein.

The data on the amounts of lipase used for immobilization on 1 g of Dowex MWA-1 and the corresponding lipase contents in the wash used during the immobilization are shown below.

TABLE 1

| Amount of lipase used | Lipase content in the wash |
|---|---|
| 1450 | 104 |
| 3060 | 378 |
| 6100 | 2325 |
| 12200 | 5426 |
| 24500 | 16054 |

It is noted from Table 1 that so long as the amount of lipase immobilized on 1 g of Dowex MWA-1 does not exceed 3060 units, about 90% of the enzyme used for the immobilization is bound to the resin and the lipase content in the used wash does not increase. Since the molecular weight of this lipase determined by the SDS electrophoresis is 120000, the amount 3060 units of the lipase is found to correspond to about $10^{-8}$M molecule of the lipase. Comparison of this number of molecules and the exchange capacity indicates that in the immobilized lipase, about $2 \times 10^5$ anion-exchange residues are existent per molecule of lipase.

The amounts of lipase up to 3060 units per 1 g of Dowex MWA-1 represent those which are sufficient for manifestation of the activity of the immobilized lipase and, at the same time, those which are incapable of impairing the reactivity when the fatty acid concentration in the reaction mixture is high.

EXPERIMENT 2

A lipase immobilized on a carrier having an anion-exchange residue and lipase incorporated therein as contemplated by this invention, a free native lipase, and a lipase immobilized on a carrier having a cation-exchange residue and a lipase incorporated therein were compared.

For the sample having a lipase immobilized on a carrier incorporating therein an anion-exchange residue and a lipase, a composite formed by binding a lipase at an amount of 1450 units per g of Dowex MWA-1 similarly to Experiment 1 was used.

As the free native lipase, a lipase prepared of *Pseudomonas fluorescens* biotype I as in Experiment 1 was used.

The carrier incorporating both a cation-exchange residue and a lipase therein was prepared as follows.

One (1) g of Lewatit CNP 80 (a macroreticular porous weakly acidic cation-exchange resin incorporating therein a carboxylic acid as an exchange group in a matrix of acrylate and having a total exchange capacity of 4.7 meq/ml, produced by Bayer AG) was combined with 50 mg of 1-cyclohexyl-3-(2-morpholinoethyl)-carbodiimide-p-toluenemethosulfonate (hereinafter referred to as "CMC") and 10 ml of water. The resultant mixture was kept at room temperature, with the pH value adjusted to 4–5 by addition of 6NHCL, to effect reaction. After the pH value was stabilized, the resultant reaction mixture was thoroughly washed to expel excess CMC. Then, the mixture was combined with 2 ml of 1/15M McIlvaine buffer of pH 4 and 50 $\mu$l of lipase solution (1450 units) and the resultant mixture was left standing overnight in a cool room, to effect reaction. Consequently, there was obtained a lipase immobilized on Lewatit CNP 80.

A lipase immobilized on Dowex MWA-1 and a lipase immobilized on Lewatit CNP 80 were tested for effect upon product inhibition by the addition of inhibitors. The effect upon inhibition of the production of fatty acid was determined by subjecting the produced glycerin to colorimetric analysis as proposed by Korn et al (J. Biol. Chem., 215, 1, (1955)).

Specifically, reactant mixtures of the same substrates as those of Experiment 1 were prepared. They were tested for lipase activity first in the absence of inhibitors and then in the presence of inhibitors, to find the ratios of the latter lipase activities to the former lipase activities taken as 100. The results are shown in Table 2.

TABLE 2

|  | Comparative Experiment | Example | Comparative Experiment |
|---|---|---|---|
|  | Standard lipase | | |
| Inhibitor | Native lipase | Lipase immobilized on Dowex MWA-1 | Lipase immobilized on Lewatit CNP 80 |
| None | 100% | 100% | 100% |
| 10% (W/V) oleic acid added | 18.1 | 89.1 | 54.3 |
| 10% (W/V) Na-oleate added | 15.1 | 86.3 | 39.0 |
| 10% (W/V) glycerin added | 100.7 | 96.1 | 83.3 |

Table 2 indicates that the native lipase was strongly inhibited by oleic acid and sodium oleate and the lipase immobilized on Dowex MWA-1 was not substantially inhibited. It further indicates that the lipase immobilized on Lewatit CNP 80 which had no anion-exchange residue on the surface was inhibited by oleic acid and sodium oleate. The activity of all the lipase preparations remained unaffected by addition of 10% of glycerin. The amount 10% of glycerin corresponds to a stoichiometric concentration in which the glycerin is produced with triglyceride having a molecular weight of about 900 is completely hydrolyzed by the reaction of three molecules of water upon one molecule of the triglyceride. The data also indicate that the lipase immobilized on the carrier through the polyfunctional reagent was relatively stable even in the presence of sodium oleate, a protein denaturating agent.

EXAMPLE 1

The lipase was immobilized on the five types of carrier described below.

(1) Controlled Poreglass (CPG 00500, having an average pore radius of 515 Å and a particle size of 120 to 200 mesh, produced by Electro-Nucleonics Inc.) was activated at 500° C. for two hours. It was then placed in an acetone solution containing 2% of silane coupling agent (3-aminopropyl triethoxy silane) and refluxed at 50° C. for 20 hours. Consequently, there was produced an anion exchanger having a primary amine residue at the terminal. By following the procedure of Experiment 2 for the immobilization using Dowex MWA-1, there was obtained lipase immobilized on the aminoalkyl CPG.

(2) By following the procedure of Experiment 2 for the immobilization using Lewatit CNP 80, the lipase was immobilized on Poreglass (carboxyalkyl CPG having an average pore radius of 547 Å and a particle size of 20 to 80 mesh, incorporating a carboxyl group at the terminal, and produced by Electro-Nucleonics Inc.).

(3) Epoxy-Toyopearl was obtained by shaking 5 g of Toyopearl HW 60 (hydrophilic vinyl polymer made by Toyo Soda) with 5 ml of 60% NaOH and 12.5 ml of epichlorohydrin at 50° C. for two hours and then washing the shaken Toyopearl with 500 ml of distilled water. This epoxy Toyopearl was combined with 12 g of hexamethylene diamine and the resultant mixture was shaken with 2 ml of 1M sodium hydroxide at 80° C. for two hours to effect reaction. The resultant reaction mixture was washed with acetone, to afford aminated Toyopearl incorporating therein a primary amine residue at the terminal. By following the procedure of Experiment 2 for the immobilization using Dowex MWA-1, the lipase was immobilized on the aminoalkyl Toyopearl.

(4) The amount 6.97 g of Cellulofine GC-700 (macroporous cellulose beads having a particle diameter of 45 to 105 μm, produced by Chisso Corp., and used as for gel filtration of proteins having a molecular weight of 100000 to 400000) was combined with 20 ml of 1N sodium hydroxide solution and 11 ml of epichlorohydrin. The resultant mixture was shaken at 30° C. for four hours to effect reaction and consequent epoxidization of the hydrophilic hydroxyl group deposited on the microporous surface of the cellulose carrier. Consequently, there was obtained epoxidized Cellulofine. Then, the epoxidized Cellulofine was washed with 500 ml of distilled water and allowed to react with 6.3 ml of ethylene diamine and 1 ml of 1N sodium hydroxide solution at 60° C. for 2.5 hours. After this reaction, the resultant reaction mixture was washed with water. The aminoethylene Cellulofine formed by the foregoing reaction was collected by suction filtration. Then, by following the procedure of Experiment 1 involved in the immobilization using Dowex MWA-1, the lipase was immobilized on the aminoethylene Cellulofine.

(5) By binding the same lipase solution of 1450 units as used in Experiment 1 with 1 g of epoxy-activated Sepharose 6B (made by Pharmacia), there was obtained lipase immobilized on agarose.

Reactant mixtures of various substrate concentrations were prepared by using beef tallow and a 0.1M phosphate buffer of pH 7.0 in Erlenmeyer flasks having an inner volume of 100 ml. In the flasks, sufficiently dehydrated immobilized lipase preparations were added and shaken at 60° C. at a rate of 178 rotations per minute to effect reaction for periods of 160 to 200 hours. The reaction time was sufficient for observation of the final ratios of conversion. The ratios of hydrolysis were calculated from the acid value and saponification value.

TABLE 3

|  | Carrier for immobilization | Final ratio of hydrolysis (%) Substrate concentration (%) | | | |
|---|---|---|---|---|---|
|  |  | 50 | 66.7 | 83.3 | 90 |
| E | Aminoalkyl CPG | 100 | 100 | 100 | 99.2 |
| C | Carboxyalkyl CPG | 68.8 | 55.9 | 53.9 | 44.7 |
| E | Aminoalkyl Toyopearl | 100.0 | 96.3 | 85.7 | 70.8 |
| E | Aminoethyl Cellulofine | 84.4 | 91.4 | 88.7 | 94.7 |
| C | Agarose | 35.7 | 66.9 | 68.0 | 68.6 |

E ... Example
C ... Comparative Experiment

Table 3 indicates that final ratios of hydrolysis of lipid at higher substrate concentrations were higher with the carriers having amino residues deposited on the surface having the lipase bound thereto than with carboxyl CPG having the carboxyl group deposited on the surface and the agarose having the hydroxyl group deposited on the surface.

EXAMPLE 2

The lipase was immobilized on various macroporous anion exchangers by following the procedure of Experiment 2 for the immobilization using Dowex MWA-1. The resultant lipase immobilized systems were subjected to hydrolysis to obtain the final ratios of hydrolysis. The anion exchangers mentioned above had anion-exchange residues deposited abundantly on the surface of their pores.

TABLE 4

| Carrier for immobilization | Final ratio of hydrolysis (%) Substrate Concentration (%) | |
|---|---|---|
| | 66.7 | 90 |
| Amberlite IRA 93 (made by Rohm and Haas) | 91.7 | 93.1 |
| Amberlite IRA 904 (made by Rohm and Haas) | 79.2 | 74.7 |
| Diaion WA 21 (made by Mitsubishi Chemical) | 72.3 | 69.4 |
| Diaion HPA 25 (made by Mitsubishi Chemical) | 91.4 | 86.5 |
| Diaion CR 20 (made by Mitsubishi Chemical) | 91.4 | 86.5 |
| Duolite A-4 (made by Diamond Shamrock Chemical Co.) | — | 85.8 |
| Duolite A-7 (made by Diamond Shamrock Chemical Co.) | — | 74.8 |
| Lewatit MP 64 (Bayer AG) | 94.9 | 92.7 |
| MP 62 (Bayer AG) | 92.0 | 71.8 |
| MP 500 (Bayer AG) | — | 85.1 |
| Sphérosil DEA (Rhône-Poulenc) | 85.6 | 84.2 |
| DEAE Sephacel (Pharmacia) | 87.5 | 62.1 |

Table 4 shows that the lipase immobilized systems having suitable amounts of lipase bound to macroporous type anion exchangers and anion-exchange type chelate resin (Diaion CR 20) hydrolzyed lipid in high substrate concentrations with high ratios of conversion because the lipase and anion-exchange residues coexisted on their surfaces.

EXAMPLE 3

By following the procedure of Experiment 2 for the immobilization using Dowex MWA-1, the lipase of *Chromobacterium viscosum* (made by Toyo Jozo Co., Ltd.) was immobilized on Sphérosil DEA (anion exchanger produced by Rhône-Poulenc) and on DEAE-Cellulofine AH (produced by Chisso Corp.).

A high acid value rice bran oil was obtained by dewaxing rice bran oil of a high acid value. The acid value and the analyses of the glyceride of the high acid value oil are shown in the first column of Table 5. The analysis of the glyceride was carried out by using a thin layer chromatography-frame ionization detector system.

An Erlenmeyer flask having an inner volume of 100 ml was charged with 1 g of the high acid value oil, 1 g of glycerin, and 0.5 g of immobilized lipase, closed tightly with a silicone rubber stopper, and shaken in a constant temperature bath at 60° C. at a speed of 133 rotations per minute for 24 hours to effect reaction. The reaction mixture was combined with a 1:1 mixture of ethanolbenzene and filtered. The filtrate was analyzed.

TABLE 5

| | High acid value oil | Lipase immobilized on Sphérosil DEA | Lipase immobilized on DEAE Celluofine |
|---|---|---|---|
| Acid value | 73.6 | 13.7 | 15.9 |
| Triglyceride | 36.0 w/w % | 15.9 w/w % | 16.6 w/w % |
| 1,3-Diglyceride | 7.9 | 18.2 | 18.0 |
| 1,2-Diglyceride | 7.7 | 20.4 | 20.9 |
| Fatty acid | 41.0 | 13.3 | 13.0 |
| Monoglyceride | 7.3 | 32.2 | 32.0 |

Table 5 indicates that, by the present invention, monoglyceride which is widely used as food quality emulsifier can be produced in a high yield from the rice bran oil of a high acid value which contains a fatty acid in a high concentration and, therefore, is not useful as edible oil. The decrease of acid value implies occurrence of a reaction of ester synthesis and the change of glyceride composition implies simultaneous occurrence of transesterification.

EXAMPLE 4

By following the procedure of Experiment 2, the lipase of *Pseudomonas fluorescens* biotype I was immobilized on Dowex MWA-1. One (1) g of the high acid value oil prepared by following the procedure of Example 3 was incubated with 0.5 g of the immobilized lipase, 0.6 g of glycerin, and 0.4 g of hexane at 60° C. for 120 hours to effect reaction. The acid value after the reaction was 29.0 in spite of the use of hexane, a nonpolar solvent which is widely used during the purification of oil.

This fact implies that the free fatty acid was incorporated into the glycerides. The synthesized glycerides contained 24% of monoglyceride.

EXAMPLE 5

By following the procedure of Experiment 2, the lipases of *Mucor japanicus* and *Rhizopus niveus* (produced by Amano pharmaceutial) and the lipase of *Pseudomonas mephitica* var. *lipolytica* (FERM-p No. 520) were severally immobilized on Dowex MWA-1. One (1) g of the high acid value oil prepared by following the procedure of Example 3 was incubated with 0.5 g of the immobilized lipase and 1 to 4 g of glycerin to effect reaction. The results were as shown in Table 6.

TABLE 6

| Origin of lipase | P. mephitica var. lipolytica | Mucor japanicus | R. niveus |
|---|---|---|---|
| Reaction conditions | 60° C., 120 hr | 40° C., 72 hr | 40° C., 72 hr |
| Acid value of reaction product | 24.6 | 14.6 | 13.0 |
| Monoglyceride content | 34.8 w/w % | 31.9 | 35.0 |

The data show that in accordance with this invention, proper selection of the lipase to be immobilized permits monoglyceride to be obtained in a high yield from the high acid value oil which contains free fatty acid in a high concentration.

EXAMPLE 6

By following the procedure of Experiment 2, the lipase of *Pseudomonas fluorescens* biotype I was immobilized on 80 g of Dowex MWA-1 to produce an immobilized lipase. Then, in a cylindrical column 1 illustrated in the drawing, olive oil was subjected to enzymatic reaction. In the drawing, 2 stands for an inner tube, 3 for a glass filter at the bottom, and 4 for an immobilized lipase column 41 mm in diameter and 195 mm in length to accommodate an immobilized lipase. An empty space 5 intervening between the inner tube and the outer shell of the cylindrical column received 60° C. water through an inlet 6 and discharged spent water through an outlet 7, to keep the immobilized lipase at 60° C.

In this example, a fine emulsion was prepared by stirring 6 parts of olive oil and 4 parts of water. This emulsion was placed to fill the immobilized lipase column. Then, the olive oil 8 was fed at a flow rate of 0.6 ml/hr upwardly into the column and the water 9 at a flow rate of 0.4 ml/hr downwardly. Consequently, a water-soluble product 10 was obtained at a flow rate of 0.4 ml/hr through the lower end of the cylindrical column and an oily product 11 at a flow rate of 0.61 ml/hr through the upper end of the cylindrical column.

Table 7 shows the reaction time and the ratio of hydrolysis of the oily product. The ratio of hydrolysis was calculated from the ratio of acid value to saponification value.

TABLE 7

| Reaction time | Ratio of hydrolysis |
|---|---|
| 116 hr | 77.4% |
| 165 | 74.6 |
| 285 | 75.0 |
| 315 | 75.1 |
| 645 | 75.2 |
| 708 | 74.2 |

In the water-soluble product obtained after 165 hours' reaction, glycerin of a concentration of 0.036 g/ml was detected. This fraction contained neither fatty acid nor glyceride at all. In contrast, in the oily product, a fatty acid and diglyceride were chiefly detected.

These results indicate that this invention enables continuous production of fatty acid in a high concentration by the hydrolysis of olive oil and continuous fractional separation of the oily product and the water-soluble product.

EXAMPLE 7

By following the procedure of Experiment 2 for the immobilization using Dowex MWA-1, the lipase of *Pseudomonas fluorescens* biotype I was immobilized on 102.5 g of Diaion HPA 25. A packed column was prepared after the pattern of Example 6. Water was fed at a flow rate of 0.4 ml/hr into the upper middle level, a 1:1 mixture of olive oil and isooctane at a flow rate of 1.2 ml/hr into the lower middle level and a water-soluble product was withdrawn at a flow rate of 0.4 ml/hr through the lower end. An oily product eluted out through the upper end. The ratio of hydrolysis of olive oil in the oily product was 92.8% after 67.7 hours' reaction and 93.2% after 102.3 hours' reaction. The main component of the hydrolyzate was fatty acid.

What is claimed is:

1. In an enzymatic hydrolysis reaction involving a fatty acid using lipase enzyme, the improvement which comprises:

bringing a reaction mixture (a) containing an oily substance into contact with a carrier (b) having a plurality of pores whose average radius is in the range of 100 to 10,000 Å, having incorporated therein a multiplicity of free anion-exchange radicals, which radicals are a chemical residue selected from the group consisting of amine compound radicals, ammonium compound radicals and derivatives thereof, having said lipase immobilized by multiple-point bonding directly and through available anion-exchange radicals on said carrier (b) so that not less than about $2 \times 10^5$ anion-exchange residues per molecule of said lipase are existent on said carrier to thereby allow the pH of said reaction mixture (a) to be on the acidic side, causing said free anion-exchange radicals of said carrier (b) to dissociate in said reaction mixture (a), which, because they are charged positively, are thereby enabled to expel cations from the microenvironment of said carrier and consequently allow the pH of said microenvironment to shift to the alkali side, the activity of said lipase to remain intact, and said enzymatic hydrolysis reaction of said fatty acid to proceed with high efficiency.

2. The method according to claim 1, which further comprises causing a polyfunctional reagent to react with said lipase immobilized on said carrier, thereby enhancing immobilization of said lipase on said carrier.

3. The method according to claim 1, wherein said carrier is a member selected from the group consisting of anion-exchange resins; glass beads, silica beads, metal powders, vinyl polymers, celluloses, and agaroses having anion-exchange residues introduced therein; porous entrapped gels having anion-exchange residues attached to the inner surface thereof; and membranes and hollow fibers having anion-exchange residues attached to the surface thereof.

4. In an enzymatic hydrolysis reaction involving a fatty acid using lipase enzyme, the improvement which comprises:

bringing an oily substance in water or an aqueous liquid (a)' into contact with a carrier (b)' having a plurality of pores whose average radius is in the range of 100 to 10,000 Å, having incorporated therein a multiplicity of anion-exchange radicals, which are a chemical residue selected from the group consisting of amine compound radicals, ammonium compound radicals and derivatives thereof, having said lipase immobilized by multiple-point bonding directly and through available anion-exchange radicals on said carrier (b)' so that not less than about $2 \times 10^5$ anion-exchange residues per molecule of said lipase are existent on said carrier to thereby allow the pH of said water or aqueous liquid (a)' to be on the acidic side as a bulk, causing said free anion-exchange radicals of said carrier (b)' to dissociate in said reaction mixture resulting from said contact, which, because they are charged positively, are thereby enabled to expel cations in the microenvironment of the carrier and consequently allow the pH of the microenvironment of the carrier to shift to the alkali side, the activity of said lipase to remain intact, and said enzymatic hydrolysis reaction of said fatty acid proceeding with high efficiency thereby inducing formation of an oily product and a water-soluble product in the reaction mixture; and thereafter separating the oily product and water-soluble product independently of each other from the reaction mixture.

5. The method according to claim 4, wherein said contact of said oily substance and said aqueous liquid substance with said carrier which contains free anion-exchange groups and said immobilized lipase, is by counterflow contact.

6. The method according to claim 5, wherein said counterflow contact is effected in a vertically erected reaction tank by supplying said oily substance to a middle lower stage of said reaction tank and said aqueous liquid substance to the middle upper stage thereof and discharging the oily substance via the upper end of said reaction tank and said water-soluble product via the lower end thereof.

* * * * *